(12) United States Patent
Weigl et al.

(10) Patent No.: US 7,011,791 B2
(45) Date of Patent: Mar. 14, 2006

(54) MICROFLUIDIC DEVICES FOR ROTATIONAL MANIPULATION OF THE FLUIDIC INTERFACE BETWEEN MULTIPLE FLOW STREAMS

(75) Inventors: Bernhard H. Weigl, Seattle, WA (US); Ronald L. Bardell, Redmond, WA (US); Andrew Kamholz, Seattle, WA (US); Matthew Munson, Seattle, WA (US); Eric Schilling, Seattle, WA (US); Kenneth Hawkins, Sammamish, WA (US)

(73) Assignee: University of Washington, Seattle, WA (US)

( * ) Notice: Subject to any disclaimer, the term of this patent is extended or adjusted under 35 U.S.C. 154(b) by 668 days.

(21) Appl. No.: 09/956,467

(22) Filed: Sep. 18, 2001

(65) Prior Publication Data

US 2002/0076350 A1 Jun. 20, 2002

Related U.S. Application Data

(60) Provisional application No. 60/269,754, filed on Feb. 16, 2001, and provisional application No. 60/233,396, filed on Sep. 18, 2000.

(51) Int. Cl.
| | |
|---|---|
| *G01N 21/00* | (2006.01) |
| *G01N 31/22* | (2006.01) |
| *G01N 15/06* | (2006.01) |
| *G01N 33/00* | (2006.01) |
| *G01N 33/48* | (2006.01) |

(52) U.S. Cl. .................. 422/58; 422/50; 422/68.1; 422/81; 422/82.01; 422/82.05; 422/82.09; 422/100; 422/101; 422/102; 422/103; 436/43; 436/52; 436/53; 436/174; 436/180

(58) Field of Classification Search .................. 422/50, 422/58, 68.1, 81, 82.01, 82.05, 82.09, 100, 422/101, 102, 103; 436/43, 53, 52, 174, 180
See application file for complete search history.

(56) References Cited

U.S. PATENT DOCUMENTS

| 5,716,852 A | 2/1998 | Yager et al. ................. 436/172 |
| 5,726,404 A | 3/1998 | Brody ....................... 200/81 R |

(Continued)

FOREIGN PATENT DOCUMENTS

| WO | WO 97/00121 | 1/1997 |
| WO | WO 97/00442 | 1/1997 |

(Continued)

OTHER PUBLICATIONS

U.S. Appl. No. 09/428,801, filed Oct. 28, 1999, Holl et al.
U.S. Appl. No. 09/428,793, filed Oct. 28, 1999, Holl et al.

(Continued)

*Primary Examiner*—Jill Warden
*Assistant Examiner*—Brian Sines
(74) *Attorney, Agent, or Firm*—Seed IP Law Group PLLC

(57) ABSTRACT

Microfluidic devices and methods are provided for enhancing detection of a diffusion pattern formed by particles diffusing between at least two fluid streams in parallel laminar flow such that an interface is formed between them by increasing the dimension of the streams in the diffusion direction. This may be accomplished by flowing the streams through a transforming turn, or by flowing the streams through a channel having diverging walls. Devices and methods are also provided for enhancing diffusion between two streams comprising changing the interface between said streams from a narrow interface to a broad interface.

13 Claims, 14 Drawing Sheets

(2 of 14 Drawing Sheet(s) Filed in Color)

U.S. PATENT DOCUMENTS

| | | | |
|---|---|---|---|
| 5,726,751 A | 3/1998 | Altendorf et al. | 356/246 |
| 5,747,349 A | 5/1998 | van den Engh et al. | 436/172 |
| 5,748,827 A | 5/1998 | Holl et al. | 385/134 |
| 5,842,787 A * | 12/1998 | Kopf-Sill et al. | 366/340 |
| 5,885,470 A | 3/1999 | Parce et al. | 216/33 |
| 5,922,210 A | 7/1999 | Brody et al. | 210/767 |
| 5,932,100 A | 8/1999 | Yager et al. | 210/634 |
| 5,948,684 A | 9/1999 | Weigl et al. | 436/52 |
| 5,971,158 A | 10/1999 | Yager et al. | 209/155 |
| 5,972,710 A | 10/1999 | Weigl et al. | 436/34 |
| 5,974,867 A | 11/1999 | Forster et al. | 73/61.41 |
| 6,007,775 A | 12/1999 | Yager | 422/57 |
| 6,077,157 A | 6/2000 | Fairbairn et al. | 454/49 |
| 6,134,950 A | 10/2000 | Forster et al. | 73/54.01 |
| 6,136,272 A | 10/2000 | Weigl et al. | 422/82.05 |
| 6,159,739 A | 12/2000 | Weigl et al. | 436/52 |
| 6,171,865 B1 | 1/2001 | Weigl et al. | 436/52 |
| 6,176,962 B1 | 1/2001 | Soane et al. | 156/292 |
| 6,221,677 B1 | 4/2001 | Wu et al. | 436/518 |
| 6,277,641 B1 | 8/2001 | Yager | 436/52 |
| 6,592,821 B1 * | 7/2003 | Wada et al. | 422/68.1 |

FOREIGN PATENT DOCUMENTS

| | | |
|---|---|---|
| WO | WO 97/12223 | 4/1997 |
| WO | WO 97/35189 | 9/1997 |
| WO | WO 97/39338 | 10/1997 |
| WO | WO 97/45644 | 12/1997 |
| WO | WO 97/47390 | 12/1997 |
| WO | WO 98/18157 | 4/1998 |
| WO | WO 98/43066 | 10/1998 |
| WO | WO 99/05512 | 2/1999 |
| WO | WO 99/17100 | 4/1999 |
| WO | WO 99/17119 | 4/1999 |
| WO | WO 99/60397 | 11/1999 |
| WO | WO 00/72020 A1 | 11/2000 |
| WO | WO 00/74850 A3 | 12/2000 |
| WO | WO 01/44667 A1 | 6/2001 |

OTHER PUBLICATIONS

U.S. Appl. No. 09/428,840, filed Oct. 28, 1999, Holl et al.
U.S. Appl. No. 09/428,839, filed Oct. 28, 1999, Holl et al.
U.S. Appl. No. 09/428,804, filed Oct. 28, 1999, Holl et al.
U.S. Appl. No. 09/428,807, filed Oct. 28, 1999, Holl et al.
U.S. Appl. No. 09/688,055, filed Oct. 28, 1999, Holl et al.
U.S. Appl. No. 09/196,473, filed Nov. 19, 1998, Yager.
U.S. Appl. No. 09/705,363, filed Nov. 3, 2000, Weigl et al.
U.S. Appl. No. 09/416,072, filed Oct. 12, 1999, Yager et al.
U.S. Appl. No. 09/503,563, filed Feb. 14, 2000, Weigl et al.
U.S. Appl. No. 09/574,797, filed May 19, 2000, Weigl et al.
U.S. Appl. No. 09/675,550, filed Sep. 27, 2000, Weigl et al.
U.S. Appl. No. 09/863,835, filed May 22, 2001, Yager et al.
U.S. Appl. No. 09/579,666, filed May 26, 2000, Yager et al.
U.S. Appl. No. 08/938,585, filed Sep. 26, 1997, Wu et al.
U.S. Appl. No. 09/501,732, filed Feb. 10, 2000, Wu et al.
U.S. Appl. No. 09/804,780, filed Mar. 13, 2001, Wu et al.
U.S. Appl. No. 09/702,645, filed Oct. 31, 2000, Weigl et al.
U.S. Appl. No. 09/346,852, filed Jul. 2, 1999, Yager et al.
U.S. Appl. No. 09/500,398, filed Feb. 8, 2000, Yager et al.
U.S. Appl. No. 09/703,764, filed Nov. 1, 2000, Weigl et al.
U.S. Appl. No. 09/335,118, filed Jun. 17, 1999, Vogel et al.
U.S. Appl. No. 09/346,717, filed Jul. 2, 1999, Brody et al.
U.S. Appl. No. 09/739,074, filed Dec. 15, 2000, Kamholz et al.
U.S. Appl. No. 09/426,683, filed Oct. 25, 1999, Weigl et al.
U.S. Appl. No. 09/724,308, filed Nov. 28, 2000, Weigl et al.
U.S. Appl. No. 09/574,930, filed May 19, 2000, Altendorf.
U.S. Appl. No. 09/464,379, filed Dec. 15, 1999, Kamholz et al.
U.S. Appl. No. 09/404,454, filed Sep. 22, 1999, Yager et al.
U.S. Appl. No. 09/723,823, filed Nov. 28, 2000, Holl et al.
Bessoth, F.G. et al., "Microstructure for efficient continuous flow mixing" (Jun. 3, 1999) Anal Commun. 36(6):213–215.
Brody, J. and Yager, P., "Low Reynolds Number Micro–Fluidic Devices" (Jun. 2–6, 1996) Solid–State Sensor and Actuator Workshop, Hilton Head, S.C. p. 105–108.
Liu, R.H. et al., "Passive Mixing in a Three–Dimensional Serpentine Microchannel" (Jun. 2000) J. Microelectromech Sys. 9(2): 190–197.
Weigl, B.H. et al., "Diffusion–Based Optical Chemical Detection in Silicon Flow Structures" (Nov. 1996) Analytical Methods and Instrumentation, $\mu$TAS 96 Special Edition, pp. 174–184.
Weigl, B.H. et al., "Fluorescence and absorbance analyte sensing in whole blood based on diffusion separation in silicon–microfabricated flow structures" (Feb. 9–11, 1997) Proc. SPIE, Advances in Fluorescence Sensing Technology III, vol. 2980, p. 171–181.
Weigl, B.H. et al., "Fluorescence and absorbance analyte sensing in whole blood based on diffusion separation in silicon–microfabricated flow structures (T–Sensors)" (Jul. 1997) Biomedical Optics, Newsletter of the Int'l Biomed. Optics, Soc., an Int'l Tech. Group of SPIE, 6(1):1–4.
Weigl, B.H. et al., "Rapid sequential chemical analysis in microfabricated flow structures using multiple fluorescent reporter beads" (Nov. 1996) $\mu$TAS 96, Conference Proceedings.
Weigl, B.H. and Yager, P., "Silicon–microfabricated diffusion–based optical chemical sensor" (Conference Proceedings Europetrode 1996) Sensors and Actuators B (Chemical) 39:1–3, Zurich, Switzerland p. 452–457.

* cited by examiner

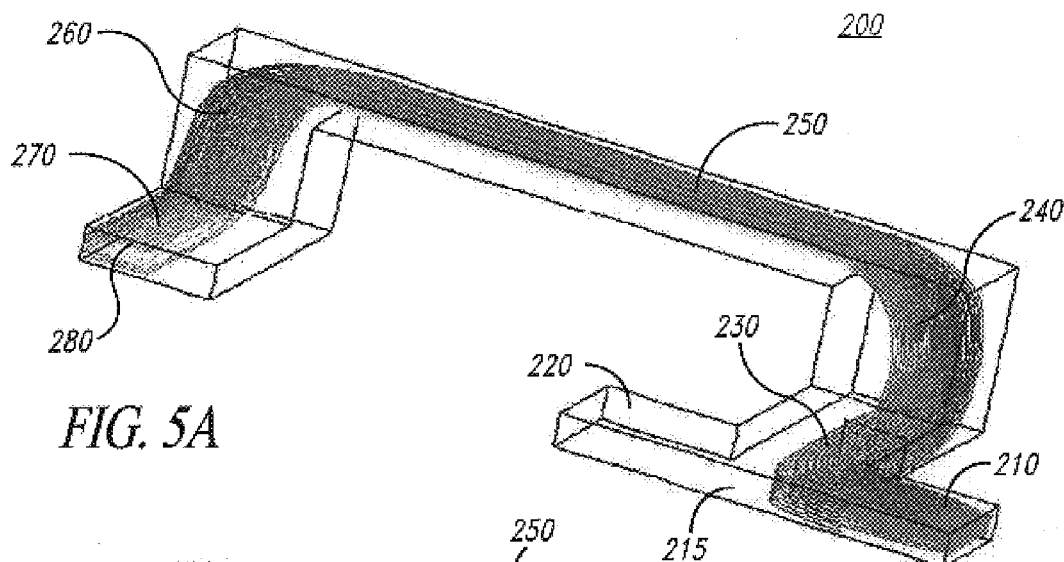
FIG. 5A
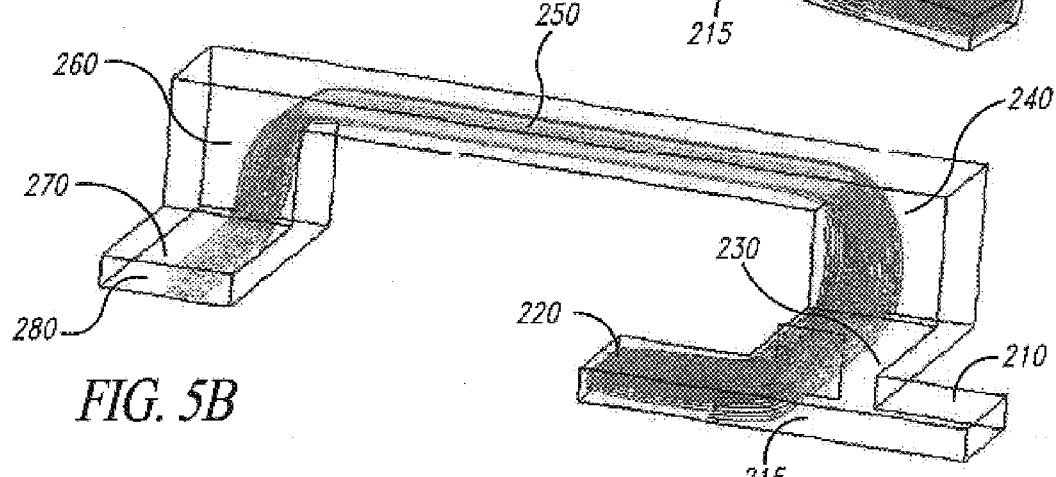
FIG. 5B
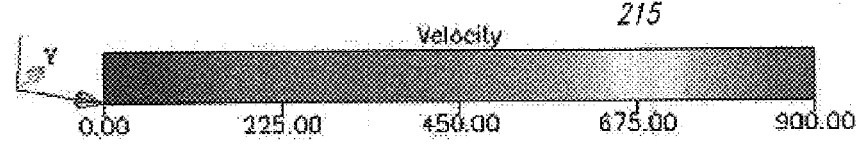

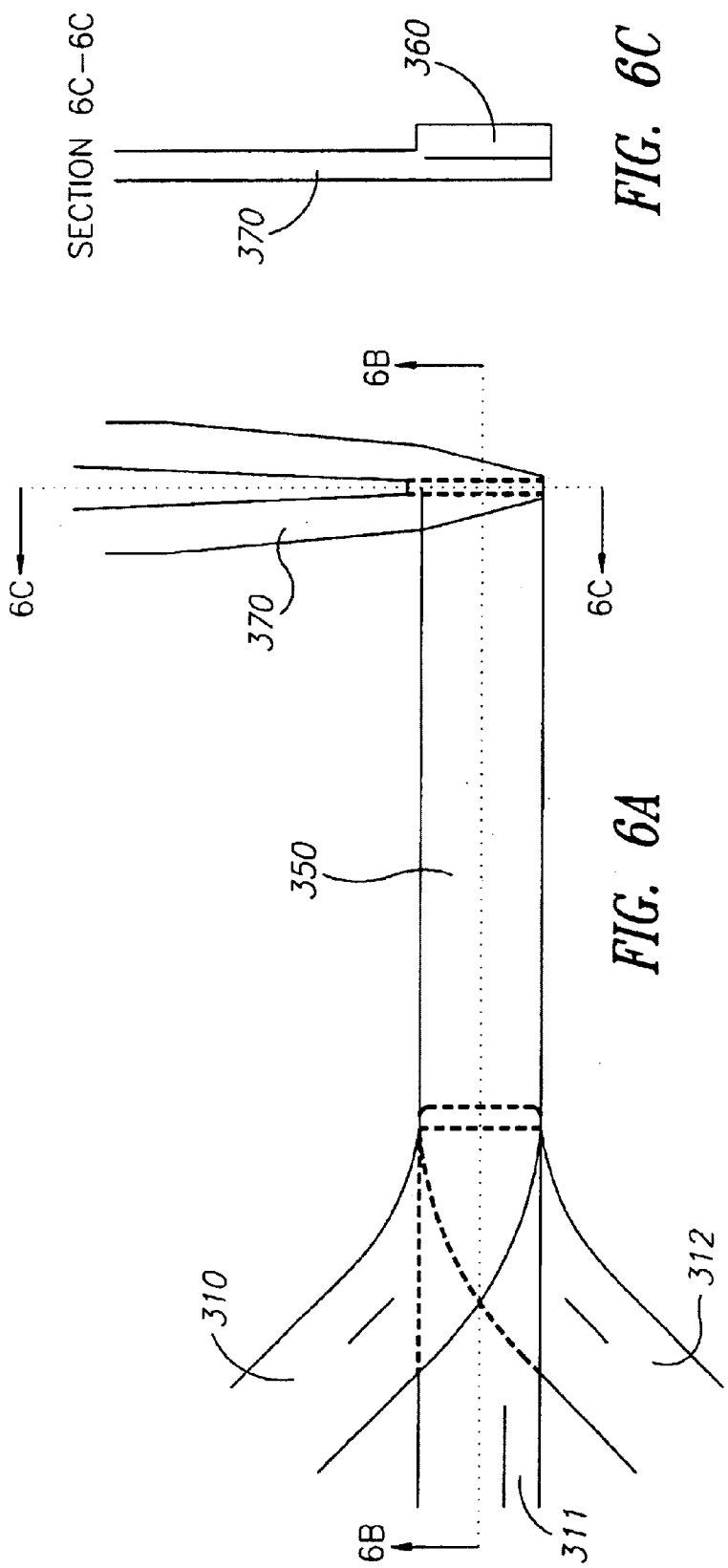
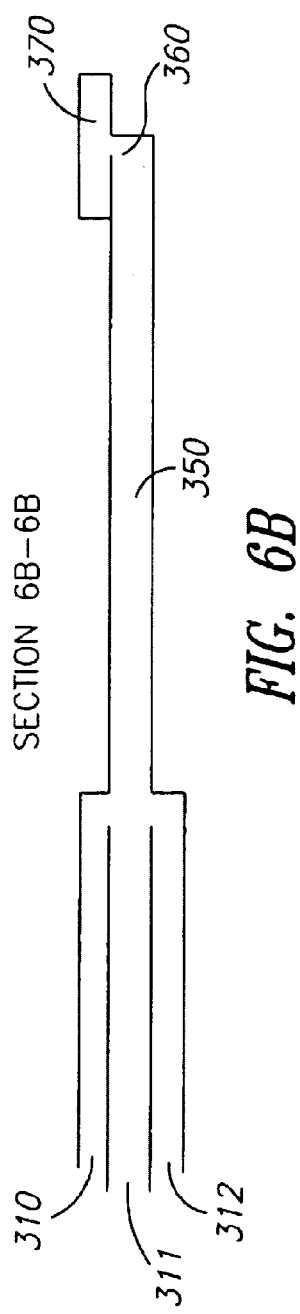
FIG. 6C
FIG. 6A
FIG. 6B

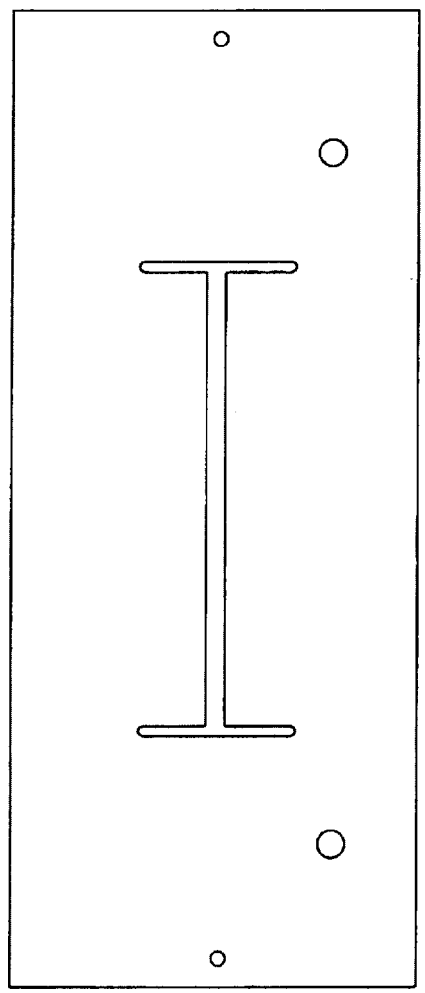
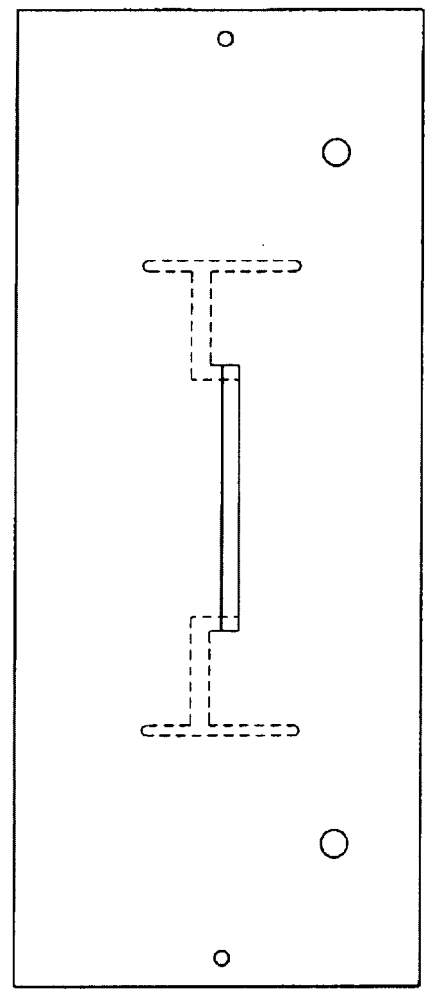
FIG.13A                    FIG.13B

MICROFLUIDIC DEVICES FOR ROTATIONAL MANIPULATION OF THE FLUIDIC INTERFACE BETWEEN MULTIPLE FLOW STREAMS

CROSS REFERENCE TO RELATED APPLICATIONS

This application claims the benefit of the filing date of U.S. Provisional Application 60/233,396 filed Sep. 18, 2000 entitled "Microfluidic Systems and Methods" and U.S. Provisional Application Ser. No. 60/269,754 filed Feb. 16, 2001 entitled "Microfluidic Devices for Rotational Manipulation of the Fluidic Interface Between Multiple Flow Streams", both of which are incorporated herein to the extent not inconsistent herewith.

FIELD OF THE INVENTION

This invention relates to microfluidic devices for analysis of liquid samples, and in particular to microfluidic devices having microfluidic channels and turns to convert the aspect ratio from one that is greater than one to one that is less than one.

BACKGROUND

Various devices and methods utilizing laminar flow and diffusion principles to detect the presence of and determine the concentration of various analytes in samples, e.g. whole blood, have been described previously. (Weigl, B. H. et al., U.S. Pat. No. 6,171,865; Weigl, B. H. and Yager, P., "Silicon-Microfabricated Diffusion-Based Optical Chemical Sensor," Sensors and Actuators B—"Europetrode" (Conference) Apr. 2, 1996, Zurich, Switzerland; Weigl, B. H., et al. "Diffusion-Based Optical Chemical Detection in Silicon Flow Structures," Analytical Methods and Instrumentation, $\mu$TAS 96 Special Edition, 1996; Weigl, B. H. et al. "Rapid Sequential Chemical Analysis Using Multiple Fluorescent Reporter Beads," $\mu$TAS 96, Conference Proceedings, 1996; Weigl, B. H. et al. "Fluorescence Analyte Sensing in Whole Blood Based on Diffusion Separation in Silicon-Microfabricated Flow Structures," SPIE Proceedings, Feb. 9–11, 1997, Fluorescence Sensing Technology III; and Brody, J. and Yager, P. "Low Reynolds Number Miro-Fluidic Devices," Solid State Sensor and Actuator Workshop, Hilton Head, S. C. Jun. 2–6, 1996)

U.S. Pat. Nos. 5,716,852; 5,972,710; 6,171,865; and PCT Patent Application Ser. No. PCT/U.S. 97105245, each of which is hereby incorporated in its entirety by reference herein to the extent not inconsistent herewith, disclose a microfabricated device comprising a laminar flow channel, at least two inlets in fluid connection with the laminar flow channel for conducting into the flow channel an indicator stream and a sample stream, and an outlet. Smaller particles in the sample stream diffuse into the indicator stream, forming a detection area wherein measurements of a detectable property are made. These three patents and the PCT application disclose methods for determining the concentration of analytes in a sample stream.

Devices such as T-sensors (e.g. U.S. Pat. No. 6,171,865) and H-filters (e.g. U.S. Pat. Nos. 6,221,677 and 5,932,100) may be used to measure a binding reaction such as that between antibodies and antigens, or between proteins and protein markers. The microfluidic device can have two or more fluid input streams in which each input stream may contain an analyte of interest, detection molecules that interact with the analyte of interest, negative and positive controls, calibration controls, or the like. These devices are designed such that all flow within the microchannels is laminar flow and cross-stream transport is by molecular diffusion.

Microchannels in such microfluidic devices may have dimensions such that the depth of the channel is less than the width of the channel, wherein width refers to the widest of the two dimensions perpendicular to the fluid flow direction. In one fluid flow configuration typical of T-sensors, the input streams travel side-by-side in parallel laminar flow having a depth less than their width, in which case diffusion occurs in the wider, widthwise dimension of the microchannel. In another configuration typical of certain perpendicular H-sensors and other microfluidic devices (e.g. U.S. Pat. Nos. 5,932,100, 6,221,677 and 6,007,775), the input streams travel as stacked ribbons, in sheet-like flow, in which case diffusion is in the narrower, depthwise dimension of the microchannel.

Microfluidic devices of this nature utilize diffusion across the fluidic interface to measure such things as protein concentrations, antigen concentrations, and diffusion coefficients. The analysis is performed by optical measurement, e.g. measurement of fluorescence intensity, across the microchannel at a particular distance downstream of the initial junction of fluid streams (Prior Art FIG. 1).

In many such systems, measurement is taken by detectors positioned to view the interdiffusion region from a position out of any plane defined by the diffusion direction, e.g. perpendicular to the direction of diffusion. In order to measure the spatial distribution of, for example, fluorescence across the x-dimension, imaging in the y-direction of side-by-side streams is required. It would not be possible to image in the x-direction (through the two streams and the interdiffusion region) without the use of more sophisticated equipment, such as a confocal microscope.

The quality of measurement, therefore, depends in part on whether enough interdiffusion of the two streams has occurred to allow good spatial resolution of the fluorescence signal. More specifically, the particular aspects of the fluorescence curves, including localized slopes, maxima, and inflection points, need to be resolved in order to perform data analysis. The quality of measurement also depends on the presence of an interdiffusion zone that is wide enough for optical measurement.

One method of improving the spatial distribution of the diffusion pattern in the interdiffusion zone is to increase the time of operation of devices in which the streams run in parallel flow. Slowing the flow rate or lengthening the channel allows more time for cross-stream diffusion to occur. However, there are several potentially prohibitive restrictions for increasing the time interval. These include the inability to achieve a low enough flow rate with a practical pumping system, the lack of practicality of fabricating a very long microfluidic channel, and the lack of clinical utility of an assay that requires a long time interval.

The amount of interdiffusion can be enhanced by using stacked, wide, sheet-like streams in which the surface area of contact between the streams is increased relative to narrower streams flowing side-by-side (e.g. U.S. Pat. Nos. 6,136,272; 6,007,775; and 6,221,677). However, while diffusion is increased using this configuration of streams, the diffusion dimension is very small and visualization is difficult.

These effects are illustrated in Prior Art FIGS. 2A and 2B and 3A and 3B in which the diffusion of an indicator dye (e.g. bromocresol purple) is followed across a channel.

FIGS. 2A and 3A indicate the amount of diffusion that has taken place in a given microchannel, while FIGS. 2B and 3B indicate the width of the resulting diffusion region. FIG. 2B shows the diffusion of 2.0 µl of dye across a 0.100 mm channel width (in the direction of diffusion) for 0.4 seconds (Diffusion coefficient=2.00 $e^{-4} mm^2/s$). FIG. 2B shows that an interdiffusion region, having a width of 60 µm is too narrow to be visually inspected when the microchannel is configured so that diffusion occurs in the narrow dimension (sheet-like flow) even though diffusion in this case is efficient (FIG. 2A).

If the diffusion channel is configured so that diffusion occurs in the wider dimension (FIG. 3) then the extent of diffusion is less than for sheet-like flow and the interdiffusion region is still only 60 µm (from 0.47 mm to 0.53 mm) as shown in FIG. 3B, which is again too narrow to be visually inspected.

If the length of the channel used to generate data for FIG. 3 is lengthened by a factor of 100, then the width of the diffusion zone is 600 µm but both the increased length of the diffusion channel and the large volume required to fill it (200 µl) are drawbacks and preclude using this method when only small quantities of fluids are available for the assay.

SUMMARY OF THE INVENTION

In its simplest form, this invention provides a microfluidic device comprising at least two inlets in fluidic connection with an interdiffusion channel (also referred to herein as a "diffusion channel") having a first aspect ratio, which is in fluidic connection with a microfluidic turn channel, which is in fluidic connection with a detection channel having a second aspect ratio. The diffusion dimension of the interdiffusion channel is less than the diffusion dimension of the detection channel.

This invention provides a microfluidic device for enhanced diffusion of two or more fluid streams combined with enhanced optical detection across the interdiffusion regions of the fluid streams. The devices of this invention may have a plurality (two or more) of inlets, microchannels, turns and outlets. This device is used to convert parallel side-by-side flow of two or more fluid streams having a "narrow interface", i.e. an interface dimension perpendicular to the flow direction which is narrower than the dimension in the diffusion direction (referred to herein as "narrow-interface streams") to ribbon, or sheet-like flow of streams having a "broad interface" i.e. an interface dimension perpendicular to the flow direction which is greater than the dimension in the diffusion direction, (referred to herein as broad-interface streams"), and/or broad-interface stream flow to narrow interface stream flow. This is accomplished by turning the fluid streams twice by about 90' within the device in such a way as to cause the fluid interface to flip from one that is narrow to one that is broad or one that is broad to one that is narrow. The diffusion dimension in the narrow-interface stream flow is greater than the diffusion direction in broad-interface stream flow. The effect of converting narrow-interface stream flow to broad-interface stream flow is to increase interdiffusion between streams by increasing the surface area of contact between the two streams. The effect of converting broad-interface stream flow to narrow-interface stream flow is to translate a highly diffused, but narrow, interdiffusion region into a region that is wide enough for optical measurement.

This invention provides for microfluidic devices comprising:

a) at least two inlets;
b) a diffusion channel in fluid communication with said inlets;
c) a transforming turn channel in fluid communication with said diffusion channel;
d) a detection channel in fluid communication with said diffusion channel;

The devices may have another transforming turn channel between the inlets and the diffusion channel.

In its simplest embodiment, this invention uses two fluid streams, however more than two streams may be used and may include, for example, sample, calibration, reference and control streams.

The devices of this invention are also designed such that all flow is laminar. In general, this is achieved in a device comprising microchannels of a size such that the Reynolds number for flow within the channel is below about 1, or in some embodiments below about 0.1. The term "laminar flow" of two streams means stable, side-by-side narrow-interface or broad-interface stream flow without mixing. There are no zones of recirculation, and turbulence is negligible.

Laminar flow is achieved in devices wherein the microchannels are of a size such that the Reynolds number for flow within the channel is below about 1, preferably below about 0.1. The Reynolds number is the ratio of inertial forces to viscous forces. A low Reynolds number means that inertia is essentially negligible, and turbulence is essentially negligible. The flow of the adjacent streams is laminar, i.e. the streams do not mix except by diffusion.

The inlets to the device need only be sized large enough to conduct the streams into narrow-interface stream or broad-interface stream laminar flow. The device may comprise microchannels less than or equal to about 5 mm in length, less than about 100 µm in depth and less than or equal to 5 mm in width. The inlets and outlets may be as long, deep and wide as required by the system of which they are a part, however, they preferably have a volume less than about 2.5 µl to accommodate small sample sizes.

The width and depth of the inlet and outlet channels must be large enough to allow passage of particles carried by the streams, preferably anywhere between about 2 or 3 times the diameter of the particles in the streams and less than or equal to about 5 mm. Particle sizes range from one or a few Å for small organic and inorganic molecules and ions to about 0.01 micrometers in depth for proteins, to about 0.1–1 micrometers for flexible long-chained molecules, to about 8 micrometers for red blood cells, to about 15 micrometers for most white blood cells, and up to about 25 micrometers for some white blood cells. The diffusion channel must additionally be large enough to allow passage of such particles, as well as adsorbent or absorbent particles which may be used in the system, and is preferably between about 2 or 3 times the diameter of such particles and less than or equal to 5 mm. The diffusion channel is most preferably less than 100 micrometers in order to achieve particle transport in a reasonable period of time. The width and depth of the diffusion channel and outlet channels must be large enough to allow passage of the particles and any other particles associated with them, such as adsorbent or absorbent particles, and are preferably between about 2 or 3 times the diameter of any absorbent or adsorbent particles present in the streams and less than or equal to 5 mm.

Aspect ratio is commonly defined as the ratio of one dimension to another. Throughout this specification, the dimensions a, b, and l are defined for the microchannels with respect to the type of flow (narrow-stream or broad-stream) present in a given microchannel. The dimension b is the channel dimension in the direction of diffusion (also referred to herein as "diffusion dimension"), l is the channel dimension in the flow direction, and a is the channel dimension that is perpendicular to both l and b. Aspect ratio is defined herein as a/b. Thus, for narrow-interface stream flow in devices of this invention, where channel depth is substantially less than channel width, b is greater than a and the aspect ratio is greater than 1. For broad-interface stream flow, b is less than a and the aspect ratio is less than 1. Thus, by converting the flow between narrow-interface stream and broad-interface stream, the device effectively acts as an aspect ratio converter.

Methods for using the microfluidic device of this invention are also provided.

Methods are also provided herein for enhancing detection of a diffusion pattern formed by particles diffusing between at least two fluid streams in parallel laminar flow such that an interface is formed between them, said method comprising:

increasing the dimension of said streams in the direction of diffusion.

This can be accomplished by flowing the streams through two transforming turns of about 90° each or by flowing the streams into a channel having diverging walls.

Methods for enhancing diffusion between at least two fluid streams in parallel laminar flow such that an interface is formed between them are also provided comprising changes between the interface between the streams from a narrow-interface to a broad-interface. This can be accomplished by flowing the streams through two transforming turns of about 90° each.

In an embodiment of this invention, three inlets are connected to an interdiffusion channel to achieve broad-interface stream flow in the diffusion channel. This broad-interface stream flow is converted to narrow-interface stream flow for optical detection. In a second embodiment, two fluid inlets are connected to an entry channel to provide narrow-stream flow of the fluid streams. This narrow-stream flow is converted to broad-interface flow for enhanced interdiffusion of the fluid streams and then converted back to narrow-interface stream flow for optical detection.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 5 A) Three-dimensional model of the aspect ratio converter device showing streak lines for fluid entering the device from the right inlet.

B) Three-dimensional model of the aspect ratio converter device showing streak lines for fluid entering the device from the left inlet.

The bar at the bottom is a key to velocities of the fluid streams in FIGS. 5A and 5B.

FIG. 6 A) top view of an aspect ratio converter in which the inlets enter directly into the interdiffusion channel.

B) cross section of 6A) through the section 6B—6B.

C) cross section of 6A) through the section 6C—6C.

FIG. 7 A) cross-sectional view of the entry channel showing relative positions of fluids from the left and right inlets.

B) cross-sectional view of the interdiffusion channel showing relative positions of fluids from the left and right inlets after the fluid has passed through the device's transforming turn channel.

FIG. 8 cross-sectional views of the A) entry channel, B) interdiffusion channel, and C) detection channel, showing the increased amount of interdiffusion expected for a prior art straight channel FIG. 9 cross-sectional views of the A) entry channel, B) interdiffusion channel, and C) detection channel, showing the increased amount of interdiffusion expected for A) and B) the aspect ratio converter device.

FIG. 10. Modeled extent of interdiffusion comparing A) a prior art T-sensor device and B) an aspect ratio converter device of this invention.

Figures 10A, 10B:
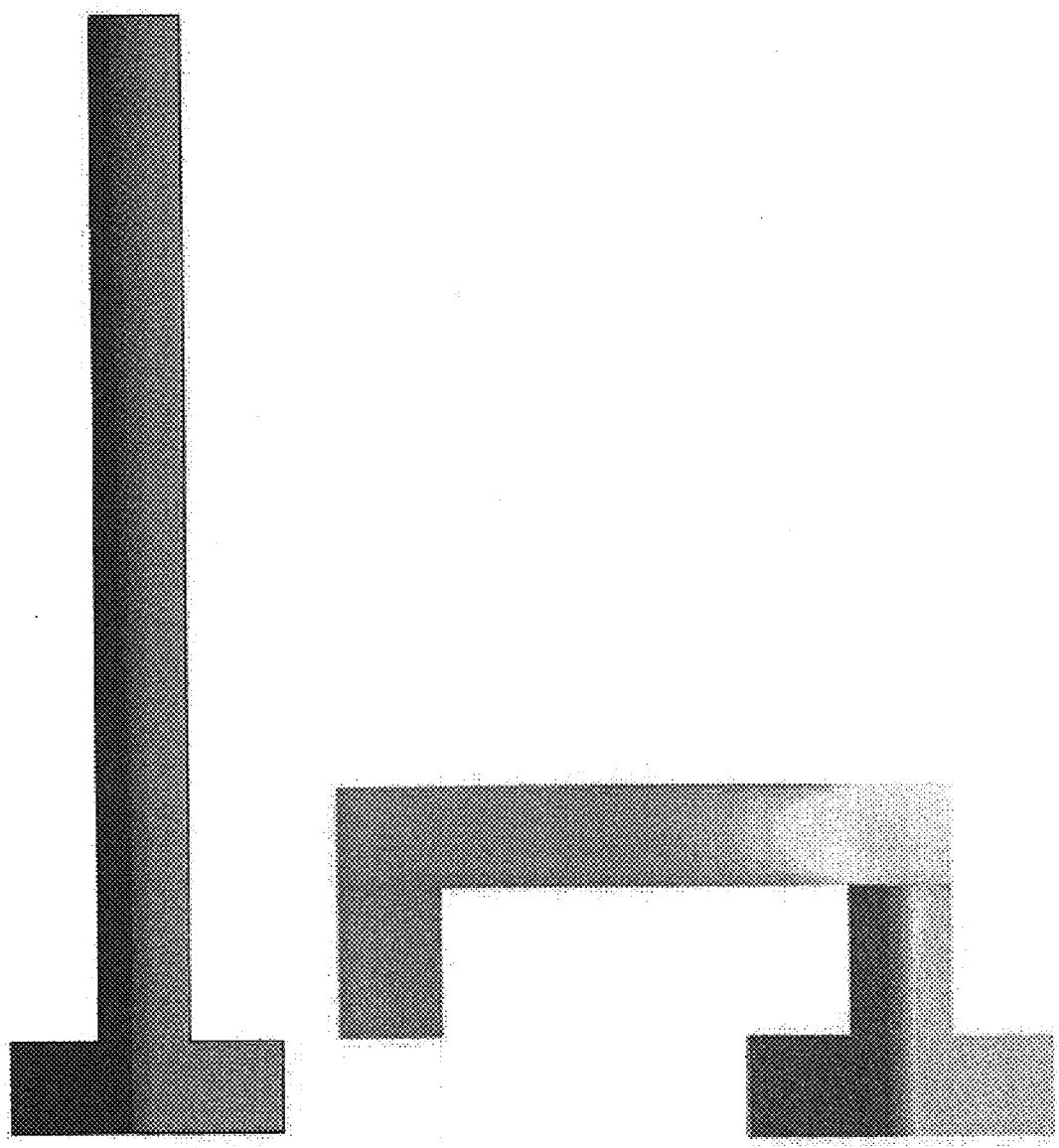
Figure 11:
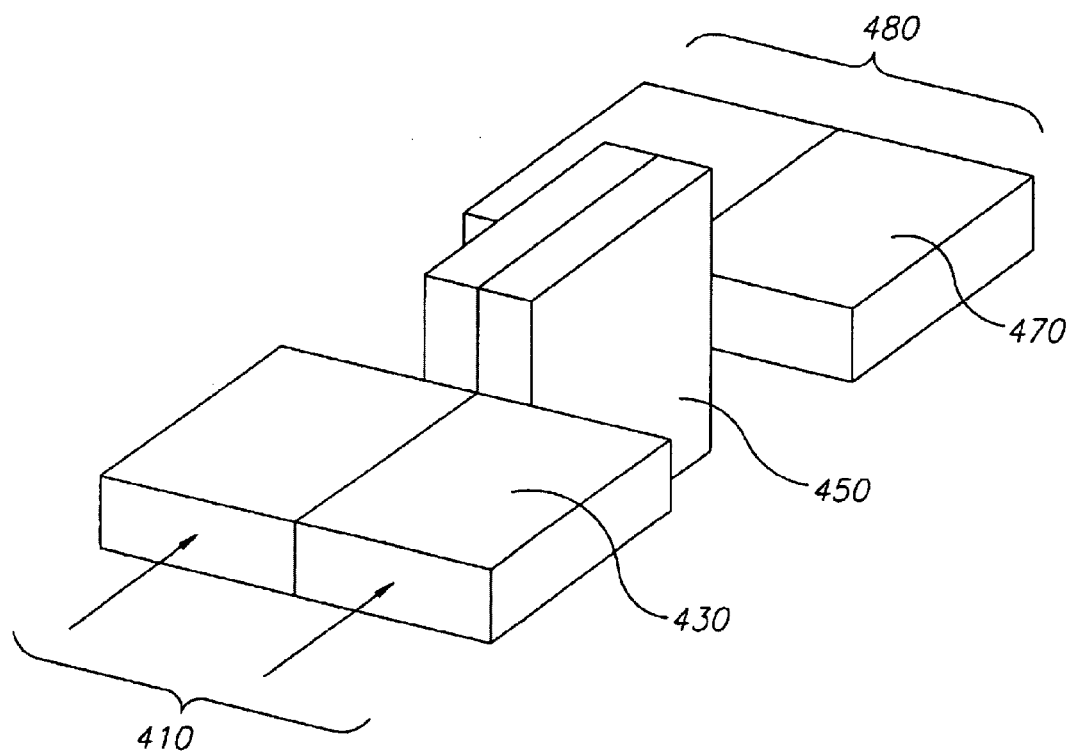

FIG. 11. Alternate geometry for a device that achieves a similar effect as the aspect ratio converter device of FIG. 10B.

Figure 12:
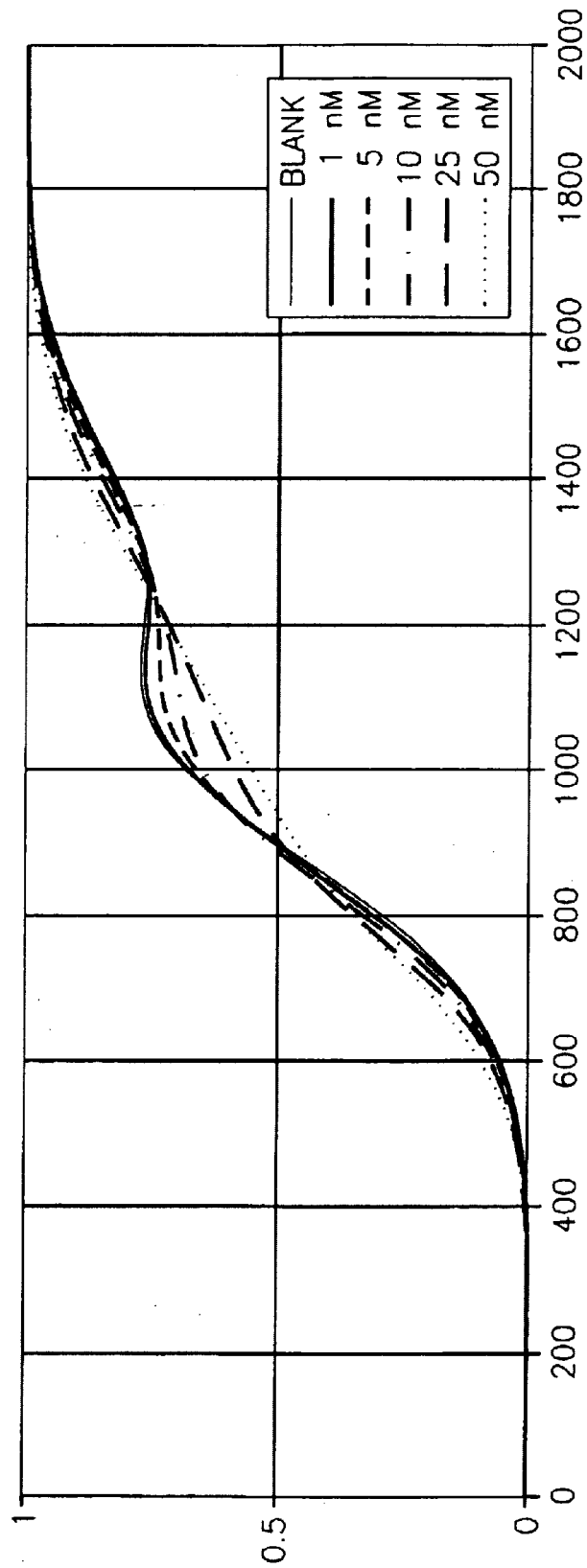

FIG. 12. Predicted fluorescence intensity curves for a diffusion immunoassay (DIA) using a straight channel.

FIG. 13. A) a prior art straight channel device and B) an aspect ratio converter device as made using plastic laminates FIG. 14. Fluorescence intensity of cells vs. diffusion distance during a cell lysis assay.

FIG. 15. Schematics of several embodiments of the aspect ratio converter device made from plastic laminates.

DETAILED DESCRIPTION OF THE INVENTION

The present invention describes a novel microfluidic channel geometry that allows manipulation of the fluidic interface between two or more flow streams to provide for improved diffusional mixing and an interdiffusion zone wide enough for visual inspection. The device disclosed herein can be used to provide for both optimal interdiffusion of fluid streams and an interdiffusion zone of sufficient size for optical measurement without increasing the time interval required for the experiment. This is achieved by manipulating the streams through a transforming turn. A "transforming turn" is a channel configuration comprising turns or bends changing the direction and plane of flow of laminar streams therein, whereby the interface go between the laminar streams is transformed from broad to narrow, or from narrow to broad, while maintaining laminar flow throughout the turn. The channel may change shape at each bend or turn to enhance the transformation of the interface between the laminar streams. Broad-interface stream flow is converted to narrow-interface stream flow or narrow-interface stream flow is converted to broad-interface stream flow and back to narrow-interface stream flow. In either case, the broad-interface stream flow is important because it results in a larger surface area of the interface between the streams relative to narrow-interface stream flow, and thus results in enhanced interdiffusion. Equally important, the conversion from broad-interface stream flow to narrow-interface flow results in a zone of interdiffusion wider than that present in broad-interface flow, which allows the interdiffusion zone to be optically measured. Importantly, the device of the present invention operates only at the low Reynolds number regime (approximately <1), thus inducing a desirable turn in the input fluids without any helical distortions. Laminar flow is maintained at all times.

The aspect-ratio conversion turns and methods of this invention may be used in the devices and methods of the following co-pending patent applications and issued patents, all of which are incorporated herein by reference to the extent not inconsistent herewith: U.S. patent application Ser. Nos. 09/428,801; 09/428,793; 09/428,840; 09/428,839; 09/428,804; 09/428,807; 09/688,055; 09/196,473; 09/705, 363; 09/416,072; 09/503,563; 09/574,797; 09/675,550; 09/863,835; 09/579,666; 08/938,585; 09/501,732; 09/804,780; 091702,645; 09/346,852; 09/500,398; 09/703,764; 09/335,118; 09/346,717; 09/739,074; 09/426,683; 09/724,308; 09/574,930; and PCT Application Numbers 99/09322; 97/10307; 98/19763; 97/21258; 97/07732; 96/09946; 97/05245; 97/04099; 97/18076; and 96/15566; U.S. Pat. Nos. 5,716,852; 5,726,404; 5,747,349; 5,748,827; 5,922,210; 5,932,100; 5,948,684; 5,972,710; 5,974,867; 6,007,775; and PCT Publications WO 98/43066 and WO 99/17119.

Figure 4:
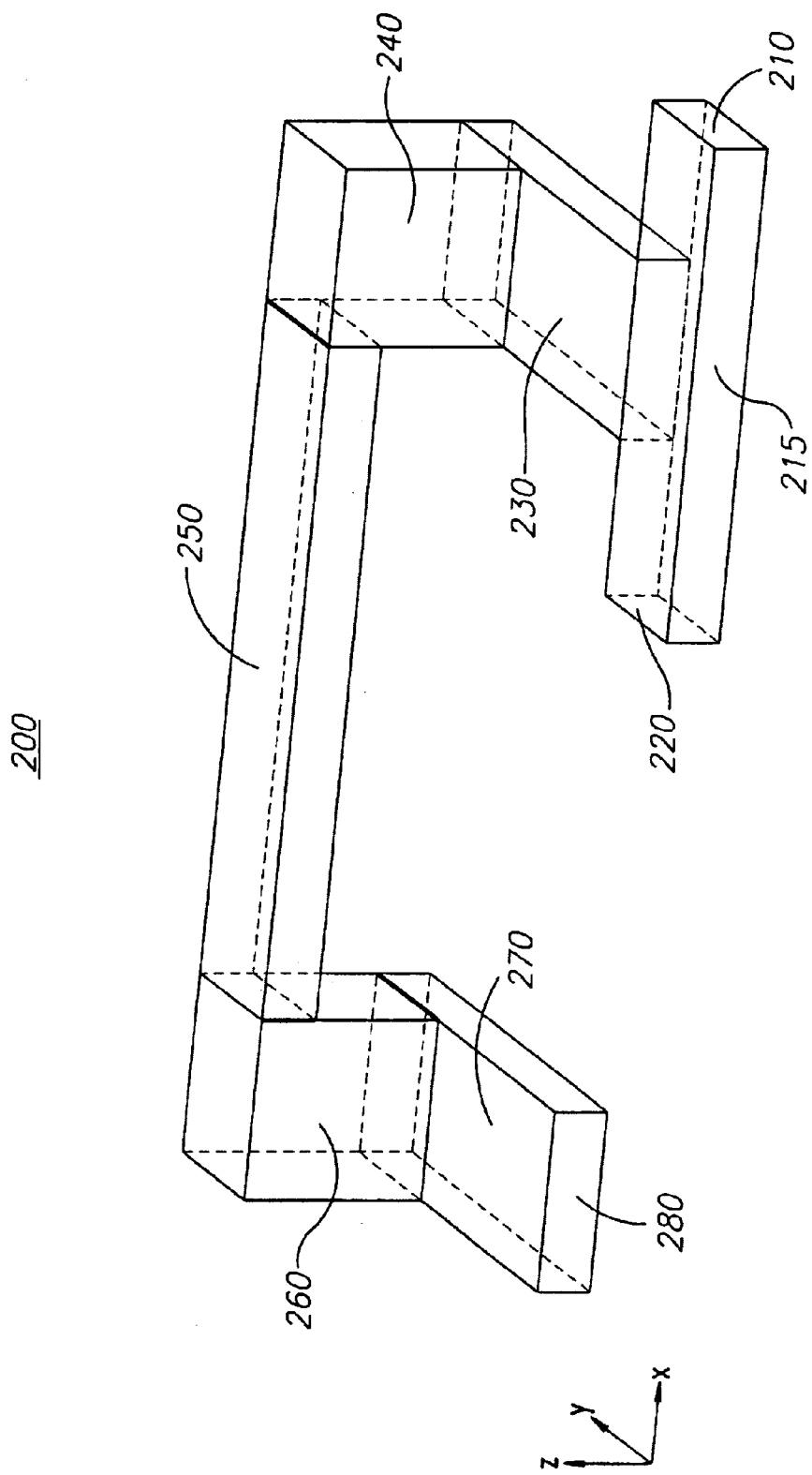
FIG. 4 Three-dimensional model of the aspect ratio converter.

One embodiment of the aspect ratio converter device of this invention is shown in FIG. 4. In this embodiment, the device comprises a right inlet 210 and a left inlet 220 in inlet channel 215 in fluidic contact with entry channel 230. Inlet channel 230 is in fluidic contact with and perpendicular to first transforming turn channel 240. First transforming turn channel 240 is in fluidic contact with and perpendicular to interdiffusion channel 250 such that interdiffusion channel 250 is also perpendicular to the direction of inlet channel 230. Interdiffusion channel 250 is in fluidic contact with and perpendicular to second transforming (reorienting) turn channel 260 in such a way that second transforming (reorienting) turn channel 260 is aligned with and parallel to first transforming turn channel 240. Second transforming (reorienting) turn channel 260 is in fluidic contact with and perpendicular to detection channel 270 such that detection channel 270 is aligned with and parallel to inlet channel 230. Fluid outlet 280 is in fluidic contact with detection channel 270.

The device of this invention operates only in the low Reynolds number regime (approximately <1). Referring to FIGS. 5A and 5B, fluids enter the device through right and left inlets 210 and 220 in inlet channel 215. The input fluids then enter the entry channel 230 where fully developed side-by-side, narrow-interface stream flow is established. As the fluids pass through transforming turn channel 240 the fluid from right inlet 210 moves from the right side of entry channel 230 to the top of interdiffusion channel 250. Similarly, the fluid from the left inlet 220 moves from the left side of entry channel 230 to the bottom of interdiffusion channel 250. This is illustrated by the use of flow trace diagrams (FIGS. 5A and 5B). Thus, the fluids are manipulated by transforming turn channel 240 such that the narrow-interface stream flow in entry channel 230 is converted to broad-interface stream flow in interdiffusion channel 250 wherein the two streams are stacked as thin ribbons. As a result, the contact area between the fluids increases relative to their contact surface area when in narrow-interface stream flow in entry channel 230. This increased contact area results in increased interdiffusion between the fluids in interdiffusion channel 250.

At the end of interdiffusion channel 250, the fluids make another turn through second transforming (reorienting) turn channel 260 after which they are returned to their original narrow-interface configuration in detection channel 270. The narrow-interface configuration allows optical analysis through the interdiffusion region along the z-axis (FIG. 4).

The device of FIG. 4 can be fabricated using laminated sheets as described in U.S. patent application Ser. No. 09/688,055.

Another embodiment of the device of this invention is illustrated in FIGS. 6A, B, and C. In this embodiment the device comprises one or more inlet channels 310, 311 and 312 in fluidic connection with interdiffusion channel 350. Interdiffusion channel 350 is in fluidic connection with and perpendicular to transforming turn channel 360. Transforming turn channel 360 is in fluidic connection with and perpendicular to detection channel 370 such that detection channel 370 is perpendicular to and in a plane parallel to interdiffusion channel 350. In use, the inlet channels 310, 311, and 312 are arranged such that the streams therein establish sheet-like laminar flow upon entry into interdiffusion channel 350. FIG. 6A also illustrates optional diverging walls of detection channel 370.

While these two embodiments describe the transforming turn channels having a rectangular transition shape, the shape of these transitions can be triangular, triangular followed by diverging walls, or any other similar shape that allows the streams to transform from narrow-interface to broad-interface flow or broad-interface to narrow-interface flow, and thus allows the aspect ratio of the channels containing flowing streams to be converted.

Figure 7A:
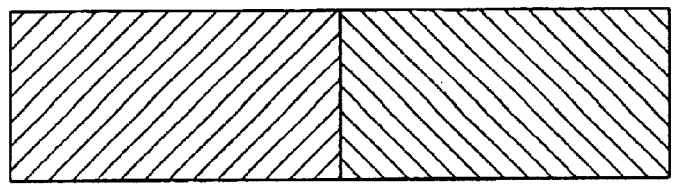
Figure 7B:
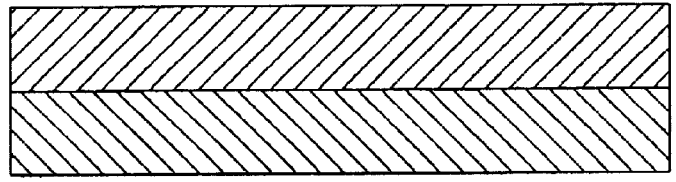

A key characteristic of the device of this invention is that the aspect ratio of the interdiffusion channels (a/b) is preferably substantially greater than one. In this disclosure, b is defined as the distance across the channel in the diffusion direction, l is the channel length in the flow direction, and a is perpendicular to b and l. The increase in contact area between the two fluids in the interdiffusion channel compared to the entry channel is proportional to the ratio of the aspect ratios of the channels. The orientation of the fluids in both the entry channel and interdiffusion channel is shown in FIG. 7. FIG. 7A shows the narrow-interface streams in the entry channel. FIG. 7B shows the broad-interface streams in the interdiffusion channel.

The effects of increased surface area contact and interdiffusion using the flip turn device of this invention relative to a conventional straight diffusion channel (e.g. the diffusion channel in a T-sensor) is further illustrated in FIGS. 8 and 9.

Figure 8A:
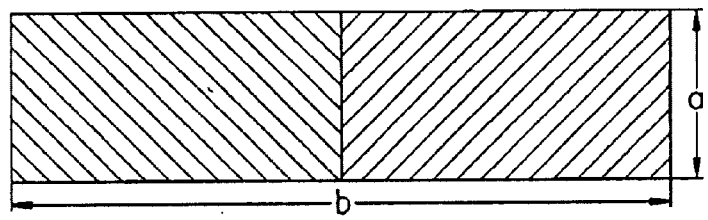
Figure 8B:
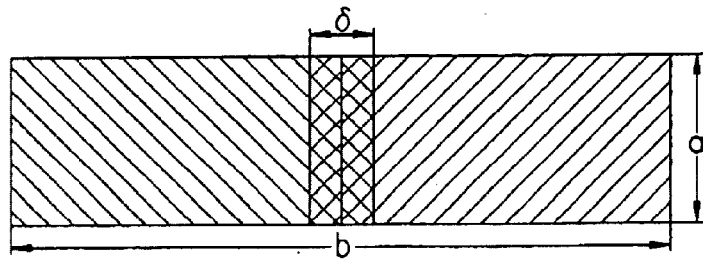
Figure 8C:
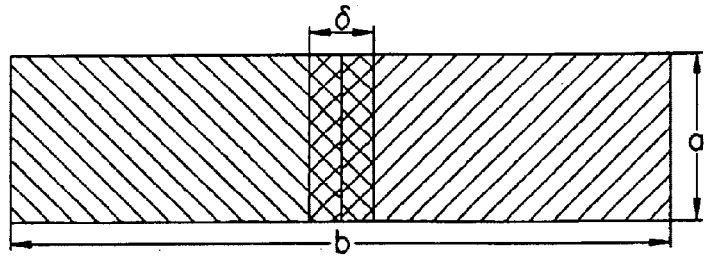

FIGS. 8A, B and C and 9A, B. and C compare the amount of interdiffusion (denoted by the distance $\delta$) expected for both a T-sensor with a straight diffusion channel (FIG. 8) and an aspect ratio converter device of this invention (FIG. 9) by comparing an interface of two fluid streams at cross-sections of the microchannels at different points along their lengths. The column of pictures in FIG. 8 depicts how the fluids behave in a straight channel without any turns. For a given flow rate and analyte, a particular amount of interdiffusion occurs and through diffusion (FIG. 8B) and detection (FIG. 8C), the fluids remain side by side.

Figure 9A:
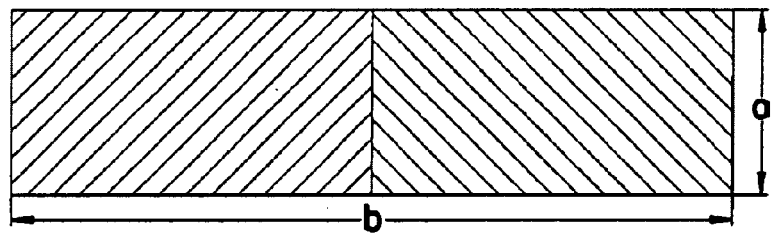
Figure 9B:
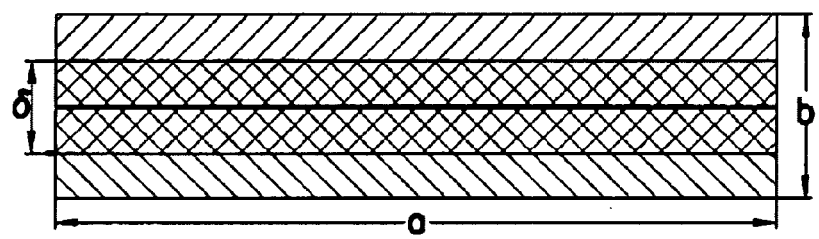
Figure 9C:
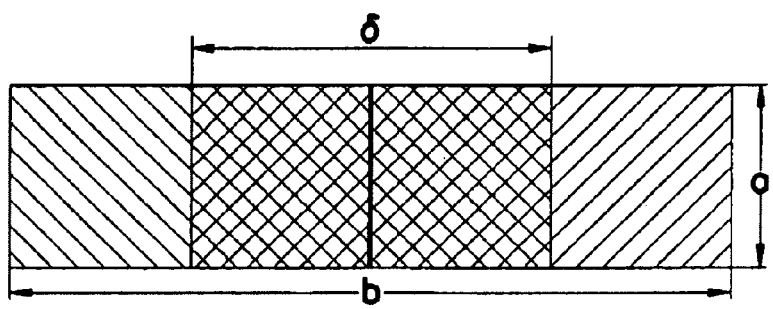

FIG. 9 depicts how the fluids behave in a device with transforming and reorienting turns (neglecting dispersion and diffusion contributions). Starting with the same initial condition at the entry (FIG. 9A), the fluid interface rotates before the interdiffusion step. Then, interdiffusion (distance $\delta$) occurs (FIG. 9B). However, it is clear that the surface area of the fluidic interface increases by a factor equal to the increase in the aspect ratio of the interdiffusion channel relative to the inlet channel. Finally, the interfaces rotate back through the reorienting turn, and the fluids are substantially more interdiffused at the detection channel (FIG. 9C).

This behavior is again illustrated in FIG. 10 which shows 3-D modeling results of interdiffusion in a straight channel vs. an aspect ratio converter device of equal lengths. In both cases, one stream contains molecules with a diffusion coefficient of $4.6 \times 10^{-6}$ cm$^2$/s (equivalent to fluorescein). The color schemes used to color FIG. 10A and FIG. 10B are different but the same interdiffusion process is occurring. It is evident that the output streams of the aspect ratio converter (FIG. 10B) are much closer to fully-mixed than the output streams of the straight T-sensor (FIG. 10A).

It is possible to achieve the same enhanced diffusion from an alternative device geometry such as that shown in FIG. 11. This device has entry channel 430 containing narrow-interface streams, in fluidic connection with interdiffusion channel 450, which is in fluidic connection with detection channel 470. In this geometry, the same increase in interface surface area can be achieved by fabricating an interdiffusion channel with a reciprocal aspect ratio relative to the entry channel.

In a simple embodiment of this invention, a single indicator or dilution stream and a single sample stream containing particles of interest are used; however, the methods and devices of this invention may also use multiple sample and/or indicator or dilution streams, and reference or calibration streams in laminar flow with each other. The preferred embodiments of this invention utilize liquid streams, although the methods and devices are also suitable for use with gaseous streams. The terms "fluid connection", "fluidic connection", and "fluidic communication" mean that elements are connected so that a fluid flowing in one element flows directly or indirectly to the other element.

The device of this invention may also be combined with other known microfluidic devices such as other analytical sensors, sheath flow assemblies and storage channels. That is, the input for the device of this invention may be the output of another microfluidic device, the output of this device may be the input for another microfluidic device, or other microfluidic device components may be incorporated into, or integrated within, the microchannel device of this invention. For example, an inlet of this device may be an outlet of another device that itself provides two or more streams already in broad-interface stream flow or narrow-interface stream laminar flow, such as the output of a T-sensor or H-filter, or the output of the device may further be in fluidic connection with a flow cytometer measuring apparatus. These are but two examples; those skilled in the art would readily recognize the advantages of integrating the aspect ratio converter device of this invention with other microfluidic devices known in the art.

Devices depicted herein may be connected in series or in parallel to provide more complex devices.

This invention further provides a microfluidic system comprising a plurality of inlets; means for controlling fluid flow through at least one of said inlets connected with said inlet; a laminar flow interdiffusion channel in fluid communication with said inlets and at least one outlet in fluid communication with said laminar flow channel. Preferably the system also comprises means for controlling fluid flow through said outlet. The microfluidic system may have a plurality of (two or more) outlets, and preferably has means for controlling fluid flow through at least one of said outlets connected with that outlet. In one embodiment of this invention, the system has two inlets. It may have two outlets, at least three, or at least four outlets. In one embodiment it has at least six inlets and at least six outlets.

Devices of this invention may include multiple inlet branches in fluid connection with the laminar flow interdiffusion channel for conducting a plurality of inlet streams into said channel. These may be arranged in a "candelabra"-like array or may be arranged successively along a "crossbar" for the "T," the branches of the "Y," or the inlet bar of the "H" configuration, the only constraint being that laminar flow of all the streams must be preserved.

Inlets include the inlet channels or "branches" and may also include other means such as tubes, syringes, and the like which provide means for injecting feed fluid into the device. Outlets include collection ports, and/or means for removing fluid from the outlet, including receptacles for the fluid, means inducing flow by capillary action, pressure, gravity, and other means known to the art. Such receptacles may be part of an analytical or detection device.

Also provided is a microfluidic system comprising a plurality of inlets; means for controlling fluid flow through at least one of said inlets connected with said inlet; a laminar flow interdiffusion channel in fluid communication with said inlets; at least three outlets in fluid communication with said laminar flow channel; and means for controlling fluid flow through at least one of said outlets connected with said outlet. In one embodiment, the system has at least four outlets, e.g., at least six inlets and at least six outlets.

Each inlet and outlet may be connected to said interdiffusion channel through inlet and/or outlet channels, an entry channel, and transforming and/or reorienting turn channels The entry channel is the channel into which one or more inlets flow. Devices in which the inlets are arranged such that sheet-like or narrow, side-by-side flow occurs immediately after the inlets may not have an entry channel.

Means for controlling fluid flow may be connected to all inlets, all outlets, all but one outlet, all but one inlet, and in a preferred embodiment are connected to all inlets and all but one outlet, or all outlets and all but one inlet.

The means for controlling fluid flow may be any means known to the art, including pressure control a means such as columns of water, electro-osmotic forces, optical forces, gravitational forces and surface tension forces. The device may further control fluid flow using internal and/or external pumps and valves known n the art. Internal pumps may include micromachined mechanical microfluidic pumps, electro-osmotic pumps and other 'onchip' pumps known in the art. External pumps such as syringe pumps and other mechanical pumps may also be used. For example, U.S. Pat. No. 5,726,404 describes pneumatic valves, check valves based on laminated layers, pinch valves, and pressure valves. The device may further include electronics or electronic interfaces for computer control of internal and external pumps and valves for controlling fluid flow.

The input streams of this invention may include sample streams containing particles to be extracted, detected or analyzed and input streams which are extraction or dilution streams. The streams may also be negative or positive controls or indicator streams. The term "particles" as used herein refers to any particulate material including molecules, cells, microspheres, suspended and dissolved particles, ions and atoms. The particles can be organic or inorganic.

The interdiffusion, or diffusion, channel is the channel of the microfluidic device in which the majority of diffusion occurs. In an aspect ratio converter device, the interdiffusion channel is the channel in which sheet-like flow is present.

The term "detection" as used herein means determination that a particular substance is present. Typically, detection also includes determining the concentration of a particular substance. The methods and apparatuses of this invention can be used to determine the concentration of a substance in a sample stream. Detection typically occurs in the detection channel of the device, which may also include a detection region. Detection may occur in any interdiffusion channel, but preferably in an aspect ratio converter device, the detection channel is after the diffusion channel and following a reorienting turn channel. Streams in the detection channel have a narrow interface. The detection region is comprised of one or more transparent windows on at least one side of the microchannel. Preferably, the transparent windows are positioned such that a light source and/or detector may be interfaced with the microchannel to measure changes in the area of diffusion between the streams. Preferably, measurement is made perpendicular to the fluid interface.

The systems of this invention may comprise external detecting means for detecting changes in an indicator substance carried within an indicator stream as a result of contact with analyte particles. Detection and analysis is done by any means known to the art, including optical and visual means such as optical spectroscopy including absorption, fluorescence, and phosphorescence spectroscopy, and light scattering; by chemical indicators which change color or other properties when exposed to the analyte; by immunological means; electrical means, e.g. electrodes inserted into the device; and by electrochemical means, radioactive means, or virtually any analytical and microanalytical technique known to the art including magnetic resonance techniques, or other means known to the art to detect the presence of an analyte such as an ion, molecule, polymer, virus, nucleic acid or nucleic acid sequence, antigen, microorganism, cell, or other factor. Furthermore, data collection may be manual or automatic and may utilize a computer or other electronic means to collect, graph, process, and analyze the data. Collectively, the apparatuses used for analytical and microanalytical techniques are referred to as "analytical measurement apparatuses." Preferably optical or fluorescent means are used, and antibodies, nucleic acid sequences and the like are attached to fluorescent markers.

Embodiments of the devices of the present invention which allow for optical measurements in transmission are provided. In such embodiments, the channel cell system, or at least an analyte detection region, may transect the width of a substrate in which the microchannels are formed. Substrate as used herein refers to the material in which the microchannels of this invention are formed, e.g., a silicon wafer or one or more plastic sheets. The detection channel, and optionally other microchannels, lie between optically transparent plates in a space which cuts through the entire width of the substrate plate.

Optical measurements exploiting reflected light are referred to herein as detection by reflection, whereas optical measurements exploiting transmitted light are referred to herein as detection by transmission.

The device of this invention may also be incorporated into an analytical cartridge for stand-alone use, or for use with an analytical instrument. Such cartridges have been described previously in, for example, U.S. patent application Ser. No. 09/688,055 which is incorporated herein in its entirety to the extent not inconsistent herewith. The cartridge can include additional valves and pumps and/or valve and pump interfaces for fluid management. It may be a self-contained, disposable cartridge having integral sample storage and waste storage containers, and may include a vent to release gases during fluid loading. The cartridge may also have alignment markings thereon to facilitate its positioning in an external instrument. For example, it may be useful to align the transparent portion(s) of the detection channel with the light sources and detectors of an external instrument. Furthermore, the cartridge may have a plurality of the devices of this invention incorporated within it and may further have other microfluidic devices such as analytical sensors (including a flow cytometric measuring device), sheath flow assemblies, T-sensors, H-reactors, storage channels, fluid reservoirs and the like in fluidic connection with the device of this invention.

The microfluidic device of this invention and any associated cartridge, may be manufactured using any microfabrication techniques known in the art and any materials for microfabrication known in the art. Materials for the manufacture of the device and/or the cartridge include silicon and other semiconductor materials, metals, glasses, ceramics, and polymers.

Common techniques in semiconductor microfabrication include LIGA, thermoplastic micropattern transfer, resin based microcasting, micromolding in capillaries (MIMIC), wet isotropic and anisotropic etching, laser assisted chemical etching (LACE), and reactive ion etching (RIE), or other techniques known within the art of microfabrication. In the case of silicon microfabrication, larger wafers will accommodate a plurality of the devices of this invention in a plurality of configurations. A few standard wafer sizes are 3", 4", 6", and 8". Application of the principles presented herein using new and emerging microfabrication methods is within the scope and intent of the claims hereof.

Preferably, the devices of this invention are made from plastics and polymers or plastic laminate layers. Known techniques for the formation of microchannels and other microfluidic features using polymers and laminate layers include laser cutting, laser ablation, and other laser methods for the selective removal of material to form microstructures within the polymer substrate, dye cutting, injection molding, and thermoforming.

Polymer materials used in the formation of the devices of this invention are known in the art, and discussed in detail, for example, in Soane, et al. (U.S. Pat. No. 6,176,962-B1), Parce et al. (U.S. Pat. No. 5,885,470) and Holl et al. (U.S. patent application Ser. No. 09/688,055), all of which are incorporated by reference herein in their entirety to the extent not inconsistent herewith. Common materials include cellulose acetate, polycarbonate, methylmethacrylate and polyester. Preferably, the device is formed from polyester Mylar™. Furthermore, layers of polymer sheets may be bonded together to form the laminate by any method known in the art, including mechanical compression, welding, or the use of adhesives. Bonding methods are discussed in detail in U.S. Pat. No. 6,176,962-B1 and U.S. patent application Ser. No. 09/688,055 both of which are incorporated by reference herein in their entirety to the extent not inconsistent herewith.

EXAMPLES

Major applications for the enhanced interdiffusion induced by the device of this invention include:

High Molecular Weight Diffusion Immunoassay

Figure 1:
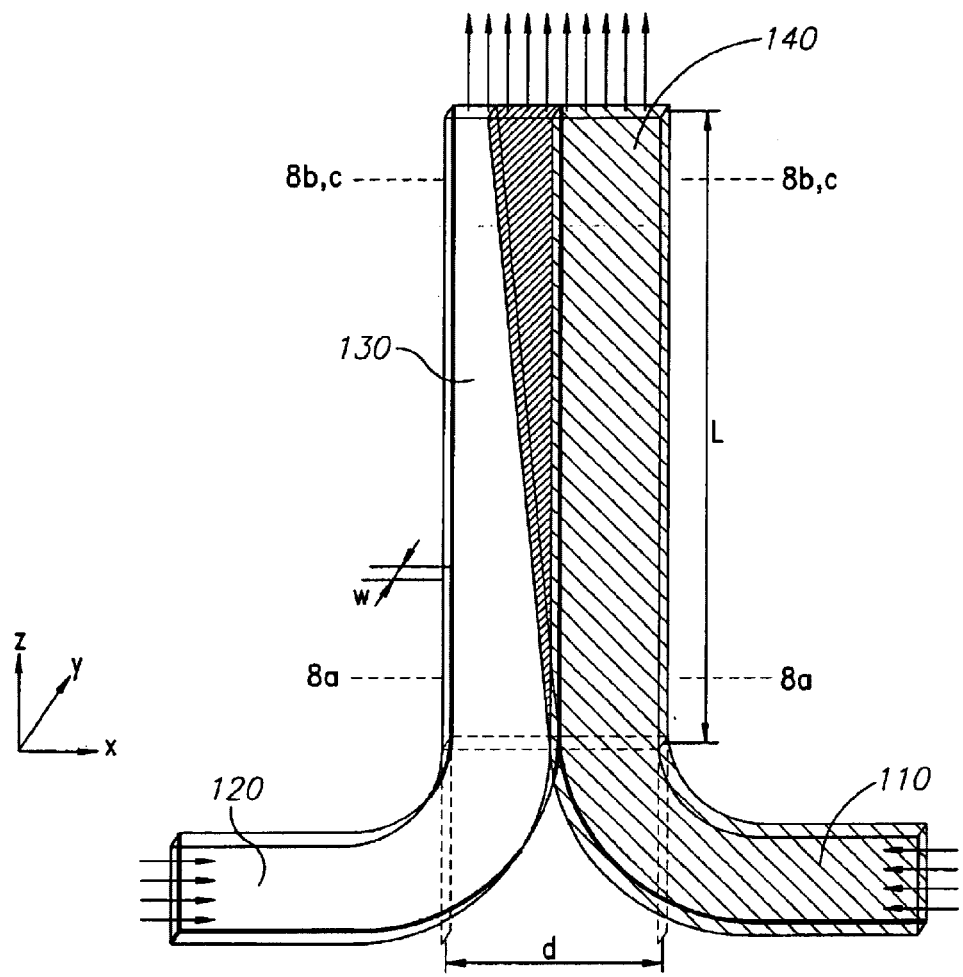
FIG. 1. Prior Art—Schematic of a T-sensor device.
Figure 2A:
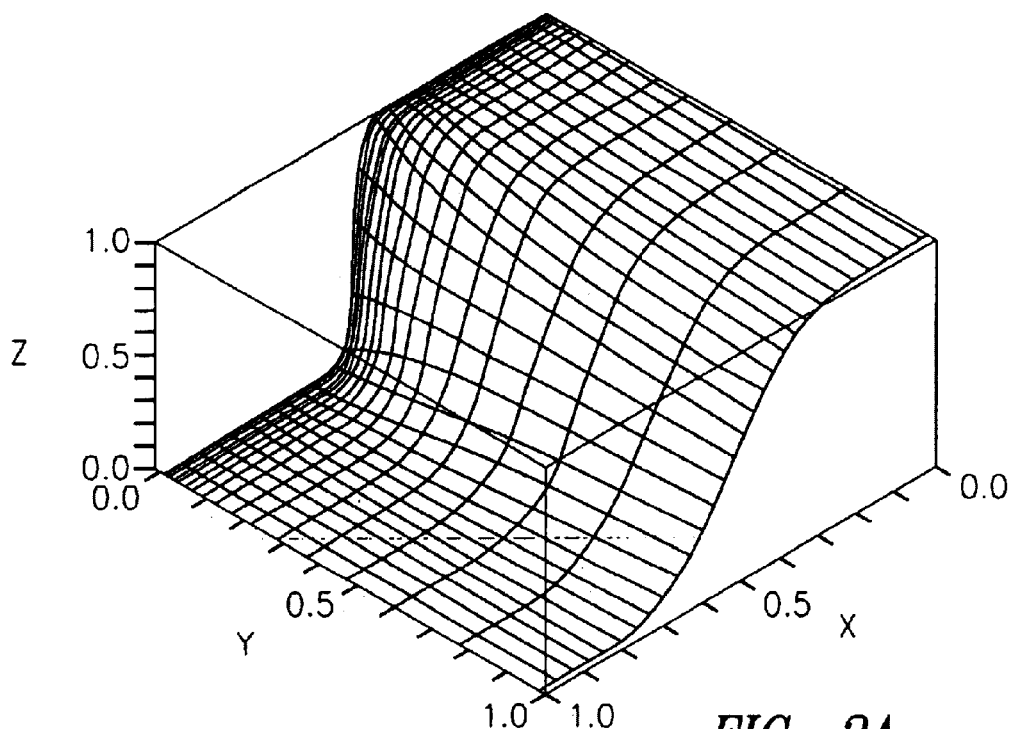
FIGS. 2A, 2B. Prior Art—Diffusion of an indicator dye in the narrow direction in an H-filter channel.
Figure 2B:
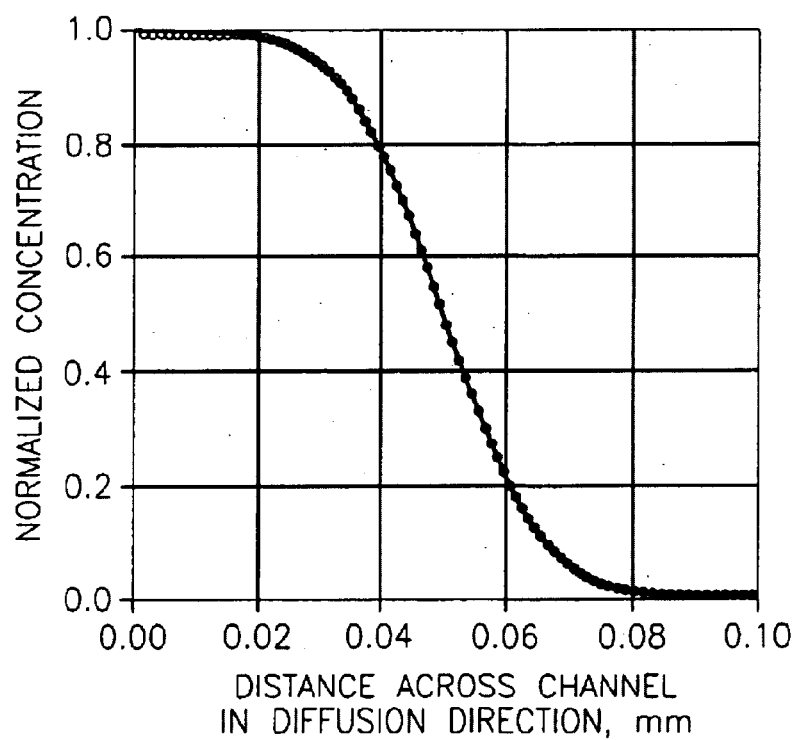
Figure 3A:
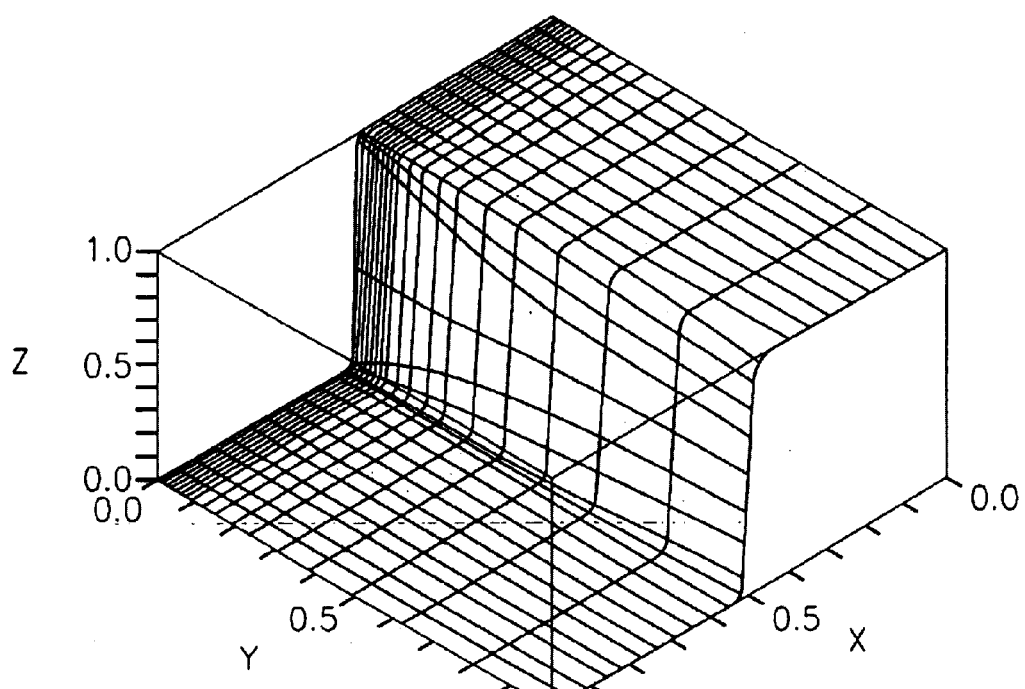
FIGS. 3A, 3B. Prior Art—Diffusion of an indicator dye in the wide direction in an H-filter channel.
Figure 3B:
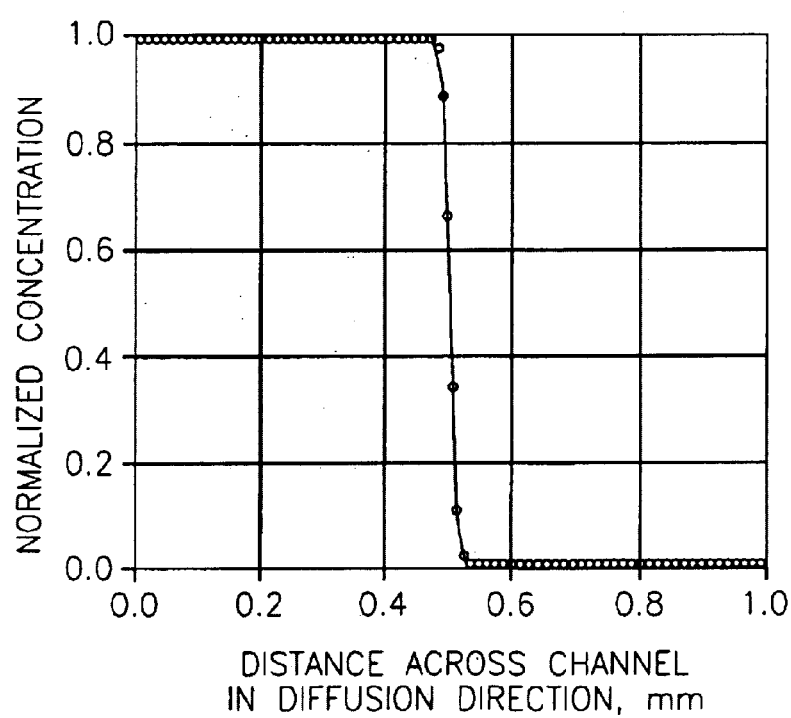

The diffusion immunoassay (DIA) is a microfluidic assay that allows measurement of the concentration of antigen in a sample. The typical orientation is similar to that of FIG. 1. One fluid contains an antibody for the antigen of interest and the other fluid is the sample spiked with a fluorescent analog of the antigen. The competitive assay relies on interdiffusion of the two fluids and interpretation of the resulting concentration profiles. The DIA has been demonstrated on a small, quickly-diffusing molecule, phenytoin. In some cases, however, it is of interest to apply the DIA scheme to larger slower-diffusing molecules. One such molecule of interest is cardiac troponin I (cTnI), an analyte thought to be a marker of cardiac infarction.

A one-dimensional model was used to predict fluorescence intensity curves that could be obtained from a DIA for cTnI using a straight channel (FIG. 12).

This set of simulations represents the most sensitive assay in the 0–50 nM range that takes no more than 10 minutes to run. Many different channel aspect ratios and reagent concentrations were tried. The simulated parameters were as follows (refer to FIG. 1):
  d=2000 µm
  w=50 µm
  L=50000 µm (5 cm)
  Flow rate=8.3 nL/s
  [antibody]=15 nM
  [fluorescent cTnI]=1 nM
  DcTnI=2.6×10$^{-7}$ cm2/s
  DAB=9.0×10$^{-7}$ cm2/s
  $K_{eq}$=1×10$^3$ nM−1
  $K_{on}$=1×10$^{-3}$ nM/s The assay time limit of 10 minutes was selected as a practical design goal based on clinical relevance. A faster assay, however, is preferable.

The need for such a long time interval is induced by the requirement that the interdiffusion zone reaches a size of several hundred microns so that the differences among the various concentration curves can be visualized. The device presented in this disclosure, however, can be utilized to greatly reduce the time needed to achieve the necessary interdiffusion zone via the mechanisms of this invention as depicted in FIG. 7B. Based on those mechanisms, the theoretical limit of improvement afforded by the new geometry is equal to the aspect ratio of the device, which is 40 in this case. Therefore, utilizing the technology of this invention reduces the run time of a 10-minute assay to as little as 15 seconds.

Low Reynolds Number Microfluidic Mixer

Many applications in microfluidics require mixing of sample and reagents. Often, time and money can be saved by performing such operations on chip instead of off chip in the hands of a technician. There are numerous ways of mixing fluids on chip. In many cases, it is desirable to perform microfluidic mixing at low Reynolds number so as not to disrupt the sample. Disruptions include unintentional cell lysis, protein denaturation, breaking of non-covalent molecular complexes, and damage to large molecules such as genomic DNA. However, low Reynolds number mixing is currently limited to diffusional mixing only, which can require a long time interval in many cases.

The technology of this invention enables more effective low Reynolds number mixing by enhancing the interdiffusion of two streams. This concept has been reduced to practice by way of an assay that reflects how much interdiffusion has occurred between two input streams.

The experiment was conducted using two devices (FIG. 13).

The two devices consisted of a traditional T-sensor (FIG. 13A) and a device of the geometry presented in this disclosure (an aspect ratio converter device, FIG. 13B). Note that FIG. 13B shows overlapped layers of a plastic laminate.

The assay measured intentional cell lysis induced by exposure to sodium dodecyl sulfate (SDS). In this experiment, 100 mM SDS and 80 mM NaCl were introduced into the left inlet. *E. herbicola* cells in 80 mM NaCl were introduced into the right inlet. The flow rate was 83 nL/sec. The cells, *E. herbicola*, were visualized by a green fluorescent stain added off-chip. When the cells lysed, a second fluorescent stain for DNA increased in intensity and quenched the first fluorophore. Therefore, a completely lysed sample shows no green fluorescence.

Both channels had a cross-sectional area of 1300 µm (across) by 100 µm (layer thickness). In both cases, the fluorescence profile (FIG. 14) was measured 3.4 cm downstream.

Figure 14:
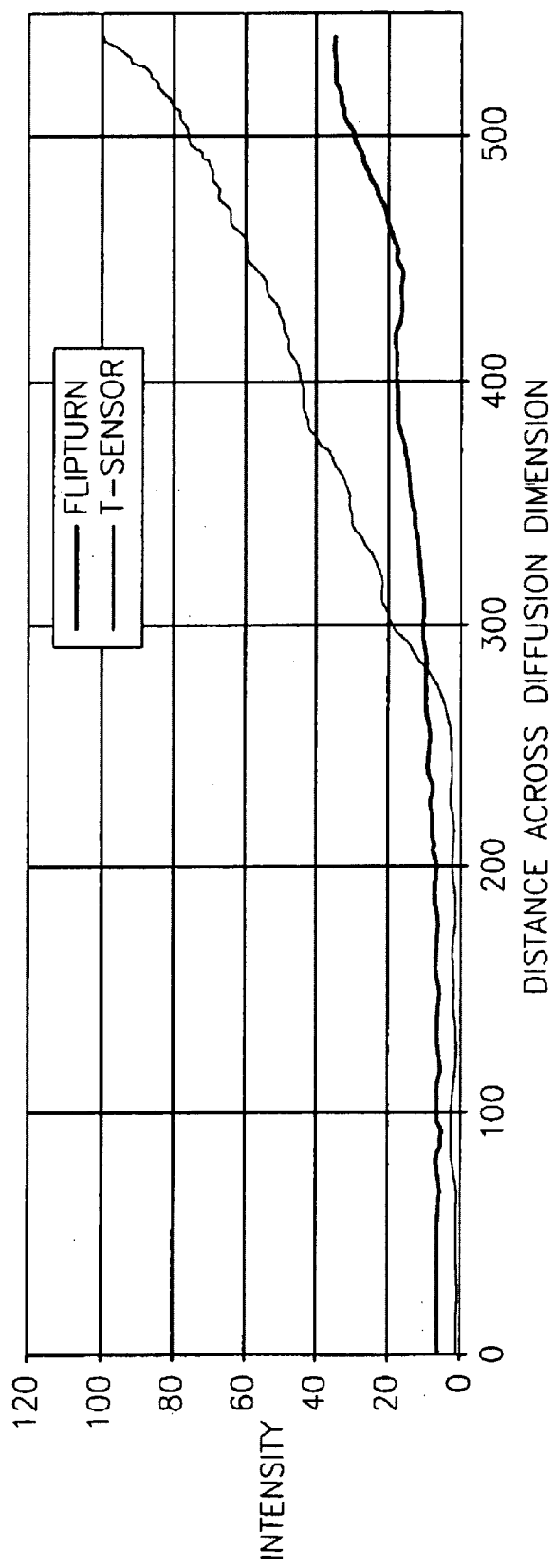
Figure 15A:
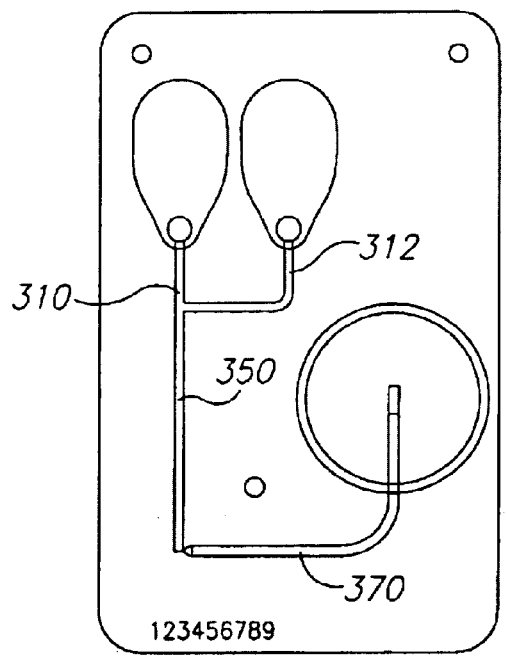
Figure 15B:
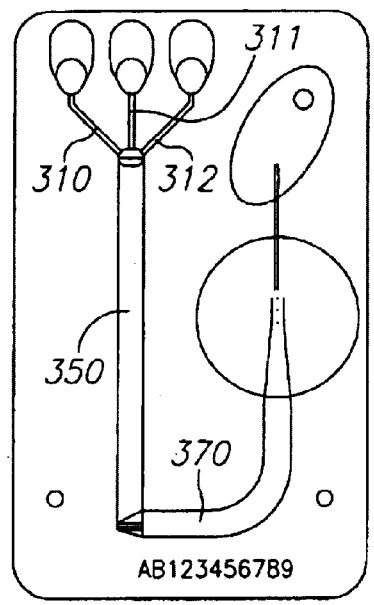
Figure 15C:
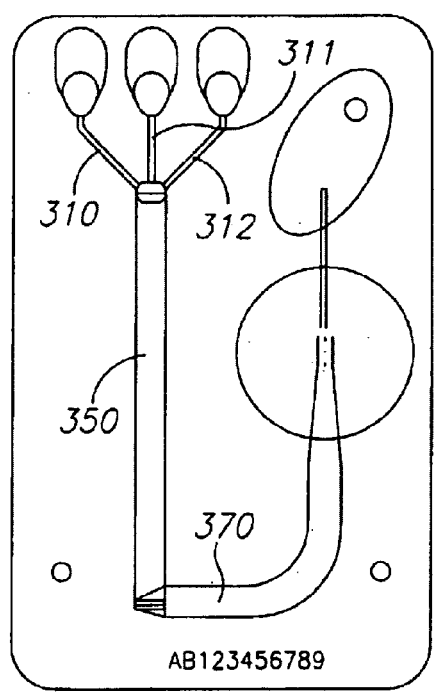
Figure 15D:
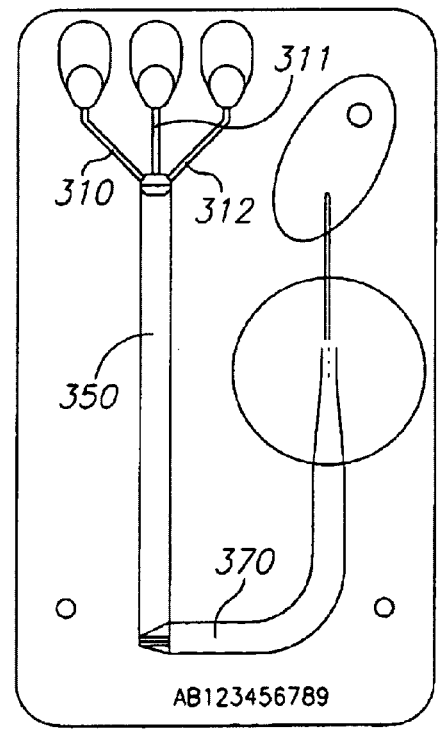

As can be seen from FIG. 14, the experiment conducted in the aspect ratio converter device produced much more interdiffusion, as indicated by lower fluorescence. In the aspect ratio converter device, a complete 90-degree rotation of the fluid interface was not seen, since the fluorescence signal in the interdiffusion channel was not uniform. This is probably due to inappropriate relative sizing of the turn geometry, as the constructed dimensions were not the same as those modeled in the three-dimensional simulation discussed above. However, some rotation was seen and the assay results were considerably improved as compared to the straight T-sensor.

All references cited herein are incorporated by reference in their entirety to the extent not inconsistent herewith.

Although the description above contains many specificities, these should not be construed as limiting the scope of the invention but as merely providing illustrations of some of the presently preferred embodiments of this invention. Thus, the scope of the invention should be determined by the appended claims and their legal equivalents, rather than by the examples given.

We claim:

1. A microfluidic device comprising:
   a) at least two inlets;
   b) a diffusion channel in fluid communication with said inlets;
   c) a first transforming turn channel in fluid communication with, and arranged perpendicular to, said diffusion channel;
   d) a detection channel in fluid communication with, and arranged perpendicular to, said first transforming turn channel,
   wherein said detection channel is arranged perpendicular to said diffusion channel.

2. The microfluidic device of claim 1 further comprising:
   a) second transforming turn channel in fluid communication with, and disposed between, said inlets and said diffusion channel; and
   b) an inlet channel in fluid communication with, and disposed between said inlets and said second transforming turn channel,
   wherein said second transforming turn channel is arranged perpendicular to said diffusion channel and said inlet channel is arranged perpendicular to both said second transforming turn channel and said diffusion channel.

3. The microfluidic device of claim 1, wherein said diffusion channel has a dimension, b, in the direction of diffusion between fluid streams flowing therein, and a dimension, a, perpendicular to both the length of said diffusion channel and to said dimension, b, and wherein the aspect ratio, a/b, of said diffusion channel is greater than 1.

4. The microfluidic device of claim 1, wherein said detection channel has a dimension, b, in the direction of diffusion between fluid streams flowing therein and a dimension, a, perpendicular to both the length of said detection channel and to said dimension, b, and wherein the aspect ratio of said detection channel, a/b, is less than 1.

5. The microfluidic device of claim 2, wherein said inlet channel has a dimension, b, in the direction of diffusion between fluid streams flowing therein, and a dimension, a, perpendicular to both the length of said inlet channel and to said dimension, b, and wherein the aspect ratio of said inlet channel, a/b, is less than 1.

6. The microfluidic device of claim 1 comprising three inlets.

7. The microfluidic device of claim 1, wherein said detection channel has diverging walls.

8. The microfluidic device of claim 1 wherein said detection channel further comprises a detection region.

9. The microfluidic device of claim 8 wherein said detection region further comprises a transparent window on at least one side of said detection channel.

10. A method for enhancing detection of a diffusion pattern formed by particles diffusing between at least two fluid streams in parallel laminar flow such that an interface is formed between them, said method comprising:

a) increasing the dimension of said streams in the direction of diffusion by flowing said streams through the microfluidic device of claim 1.

11. A method for enhancing detection of a diffusion pattern formed by particles diffusing between at least two fluid streams in parallel laminar flow such that an interface is formed between them, said method comprising:

a) increasing the dimension of said streams in the direction of diffusion by flowing said streams through a channel having diverging walls perpendicular to said direction of diffusion.

12. The method of claim 10 also comprising detecting said diffusion pattern from a point outside the plane of flow and outside the plane of the interface between said streams.

13. The method of claim 11 comprising detecting said diffusion pattern from a point perpendicular to said direction of diffusion.

* * * * *

UNITED STATES PATENT AND TRADEMARK OFFICE
CERTIFICATE OF CORRECTION

| | | |
|---|---|---|
| PATENT NO. | : 7,011,791 B2 | Page 1 of 1 |
| APPLICATION NO. | : 09/956467 | |
| DATED | : March 14, 2006 | |
| INVENTOR(S) | : Bernhard H. Weigl et al. | |

It is certified that error appears in the above-identified patent and that said Letters Patent is hereby corrected as shown below:

<u>Title Page</u>
Item (56), References Cited, Other References, page 2, "U.S. Appl. No. 09/688,055, filed Oct. 28, 1999, Holl et al." should read as -- U.S. Appl. No. 09/688,055, filed Oct. 13, 2000, Holl et al.--

Signed and Sealed this

Eighth Day of August, 2006

JON W. DUDAS
*Director of the United States Patent and Trademark Office*